(12) United States Patent
Tanner et al.

(10) Patent No.: US 8,562,635 B2
(45) Date of Patent: Oct. 22, 2013

(54) DEVICE FOR CONVERTING A ROTARY MOTION INTO AN OSCILLATING MOTION

(75) Inventors: Peter Tanner, Bubendorf (CH); Nils Schmuckli, Tenniken (CH)

(73) Assignee: Depuy Synthes Products, LLC, Raynham, MA (US)

( * ) Notice: Subject to any disclaimer, the term of this patent is extended or adjusted under 35 U.S.C. 154(b) by 1820 days.

(21) Appl. No.: 11/178,195

(22) Filed: Jul. 7, 2005

(65) Prior Publication Data
US 2005/0283175 A1 Dec. 22, 2005

Related U.S. Application Data

(63) Continuation of application No. PCT/CH03/00006, filed on Jan. 9, 2003.

(51) Int. Cl.
*A61B 17/14* (2006.01)
(52) U.S. Cl.
USPC .......................................... 606/178; 606/82
(58) Field of Classification Search
USPC .................. 606/170, 177, 178, 82; 83/824
See application file for complete search history.

(56) References Cited

U.S. PATENT DOCUMENTS

| | | | |
|---|---|---|---|
| 3,103,069 A | 9/1963 | Gary | |
| 4,069,824 A | 1/1978 | Weinstock | |
| 4,281,457 A | 8/1981 | Walton, II | |
| 4,509,511 A | 4/1985 | Neufeld | |
| 4,922,612 A * | 5/1990 | Greenwood | 30/166.3 |
| 5,201,749 A * | 4/1993 | Sachse et al. | 606/177 |
| 5,658,304 A | 8/1997 | Lim | |
| 6,033,421 A * | 3/2000 | Theiss et al. | 606/186 |
| 6,183,432 B1 * | 2/2001 | Milo | 604/22 |

FOREIGN PATENT DOCUMENTS

| | | |
|---|---|---|
| DE | 1491219 | 6/1969 |
| DE | 4425456 A1 | 3/1996 |
| EP | 1 175 870 A1 | 1/2002 |
| JP | 2002-102235 A | 9/2002 |

* cited by examiner

*Primary Examiner* — Ryan Severson
*Assistant Examiner* — Julie A Szpira
(74) *Attorney, Agent, or Firm* — Fay Kaplun & Marcin, LLP

(57) ABSTRACT

A device for converting a rotational movement into a rotatively oscillating movement is described comprising a drive shaft, a second, rotatively oscillating shaft, a driving mechanism, a housing, and a gearing mechanism comprising a movable lever. A sawing device is also described.

15 Claims, 3 Drawing Sheets

DEVICE FOR CONVERTING A ROTARY MOTION INTO AN OSCILLATING MOTION

CROSS-REFERENCE TO RELATED APPLICATIONS

This is a continuation of International Application No. PCT/CH03/00006, filed Jan. 9, 2003, the entirety of which is incorporated by reference herein.

FIELD OF THE INVENTION

The invention relates to a device for converting a rotary motion into an oscillating motion, as well as to a sawing device for working on bones.

BACKGROUND OF THE INVENTION

Gear mechanisms, which convert rotary motions of a drive shaft into a back and forth motion, have long been used in surgery, for example, for motor-driven saws. They can, however, also be used for a plurality of other technical applications.

A gear mechanism, which converts a rotary motion of a drive shaft into a back and forth motion, is known from the WO 96/27093 of TANNER. This known gear mechanism comprises an axially disposed lever, which is mounted centrally at the housing, so that it can be rotated about an axis of rotation perpendicular to the longitudinal axis, is driven at one of its ends so as to oscillate about the axis of rotation by a cam, which is disposed eccentrically at the end of the drive shaft, and, at its other end, drives the tool carrier in an oscillating manner over a further cam. The axial arrangement of the lever, so that the longitudinal axis of the oscillating shaft is at right angles to the longitudinal axis of the drive shaft, is a disadvantage of this known device.

SUMMARY OF THE INVENTION

The invention is to provide a remedy here. It is an object of the invention to create a device, which has a gear mechanism for converting a rotary motion into an oscillating motion and in which the two shafts are arranged with coaxial longitudinal axes.

Pursuant to the invention, this objective is accomplished with a device for converting a rotary motion into an oscillating motion, as well as with a sawing device for working on bones.

The advantages, achieved by the invention, are to be seen essentially therein that, due to the inventive device, a compact construction of the device is made possible since, because of the coaxial shafts, the external diameter of the housing can be kept small.

In the preferred embodiment of the inventive device, the lever of the gear mechanism is disposed transversely to the longitudinal axis of the drive shaft.

In a different embodiment of the inventive device, a hole is drilled through the drive shaft and the second shaft coaxially with their longitudinal axis. By these means, the following advantages can be achieved: a guide wire can be introduced into the coaxial central boreholes and by mounting a guide wire at the bone and introducing this guide wire into the central boreholes, an exact positioning as well as a coaxial displacement of the saw blade at the bone becomes possible.

In yet a further embodiment of the inventive device, the second oscillating shaft comprises at its rear end a catch, which is disposed eccentrically to the longitudinal axis of the shaft and can be brought into engagement with a guide at one end of the lever. The lever is mounted rotatably at the pivot and, with a second guide, mounted at the other end of the lever at a fixed cam at the housing. Preferably, the lever is mounted with its middle segment rotatably at the pivot. Due to this arrangement of the guides and the mounting at the pivot, large angles of rotation can be achieved for the oscillating shaft in spite of a short lever.

The catch has a central axis, which is at a distance "a" from the second, oscillating shaft, measured perpendicularly to the longitudinal axis of this shaft. Furthermore, the axis of the pivot has an eccentricity e to the drive shaft, measured perpendicularly to the longitudinal axis of this shaft. The ratio between the eccentricity e and the distance "a" is between 0.01 and 0.5. The cam, fixed in the housing, has a central axis, which is at a distance b from the drive shaft, measured perpendicularly to the longitudinal axis of the drive shaft, the ratio between the distance b and the distance "a" preferably being between 0.5 and 2.0.

In a preferred embodiment of the inventive sawing device, the latter comprises, aside from a device for converting a rotary motion in to an oscillating motion of one of the embodiments described above, a saw blade, which can be fastened detachably at the front end of the second shaft, as well as means for detachably fastening the saw blade at the front end of the second shaft.

In a different embodiment, the saw blade is configured as a hollow cylindrical shell piece with an external shell surface, which is coaxial with an external shell surface, and has a cross-sectional area of a annular segment, orthogonal to the longitudinal axis with a central angle β (Halgus-Valgus saw blade). Usually, the central angle β preferably is between 45° and 80°.

In yet another embodiment, a scale, on which the depth of the saw cut, which has been produced, can be read, is mounted on the external shell surface of the saw blade parallel to the longitudinal axis.

In a further embodiment, the sawing device additionally comprises a guide wire, which can be passed through the central boreholes of the drive shaft and of the second shaft. The method, which can be carried out by this embodiment, is characterized by the following steps: (a) setting the guide wire at a bone or bone fragment in such a manner, that the central axis of the guide wire passes through the center of the circular arc-shaped saw cut, which is to be carried out; (b) introducing the guide wire into the central boreholes of the drive shaft and of the second shaft of the device described above; (c) shifting the device on the guide wire coaxially with the central axis of the guide wire until the front end of the saw blade touches the surface of the bone or bone fragment, on which work is to be carried out; and (d) making the saw cuts by shifting the device further axially.

In yet another embodiment, the guide wire has an axial stop at a particular length measured from its tip, as a result of which the axial movement of the second shaft towards the tip of the guide wire and, with that, the depth of the store cut is limited.

In a different embodiment, the second shaft, at its front end, has means for detachably fastening the saw blade. These means can be in the form of a bayonet catch or a screw connection for detachably fastening the saw blade.

BRIEF DESCRIPTION OF THE DRAWINGS

The invention and further developments of the invention are described in even greater detail in the following by means of the partly diagrammatically representation of several examples.

DETAILED DESCRIPTION OF THE INVENTION

Figures 1, 2:
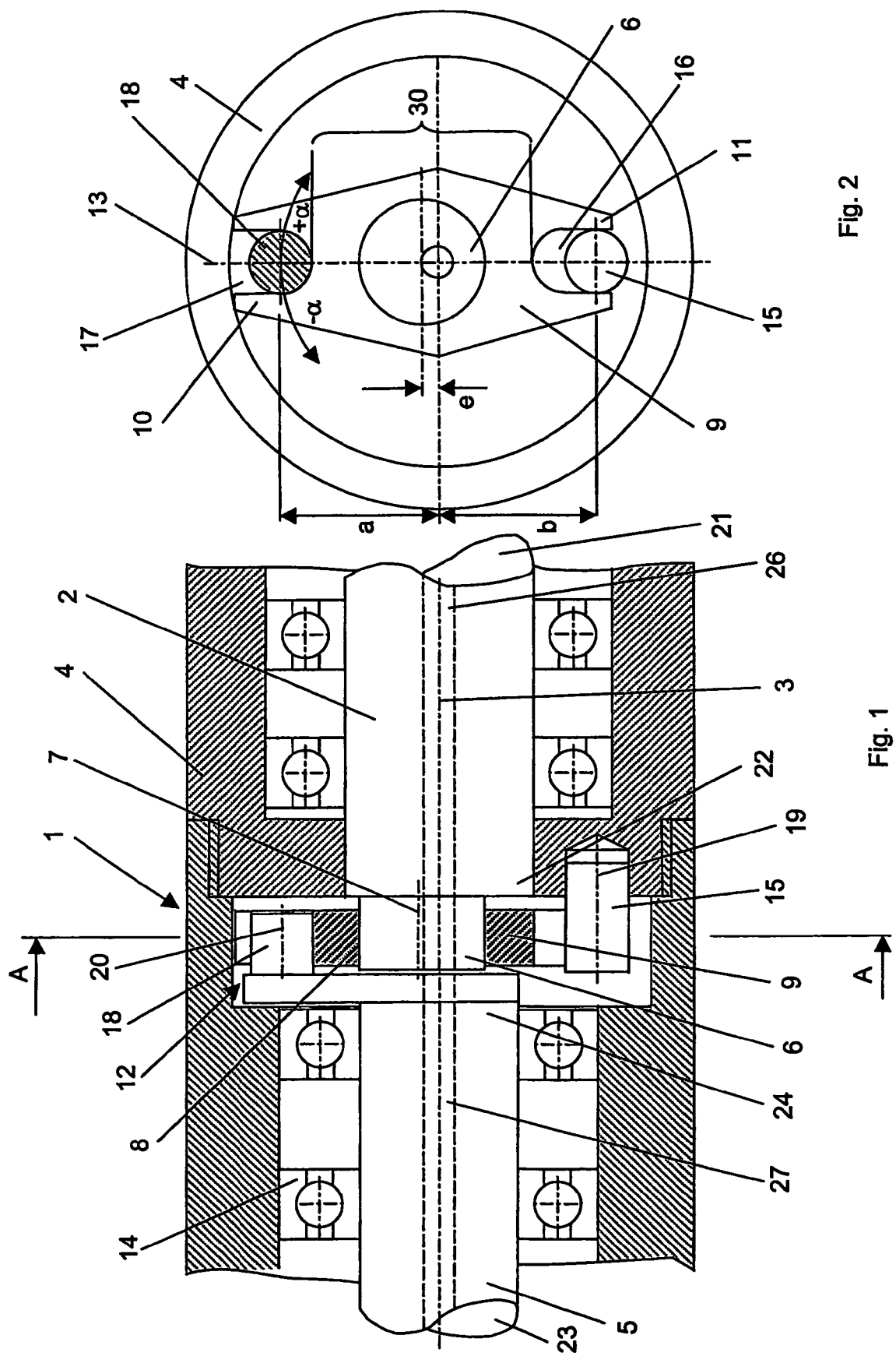
FIG. 1 shows a longitudinal section through an embodiment of the inventive device.
FIG. 2 shows a section A-A through the embodiment of the inventive device, shown in FIG. 1.

The embodiment of the inventive device, shown in FIGS. 1 and 2, essentially comprises a drive shaft 2, which rotates about the longitudinal axis 3 and can be connected with a drive unit (not shown), a second shaft, which can be connected at the end with a saw blade (FIG. 4) and is disposed coaxially with the longitudinal axis 3 of the drive shaft 2, as well as a gear mechanism 1, which is disposed between the two shafts 2; 5. The drive shaft 2 and the second shaft 5 are mounted coaxially with the longitudinal axis 3 in a multipart housing 4 axially fixed and rotatable by means of antifriction bearings about the longitudinal axis 3. It is also possible to mount one or both shafts 2; 5 in the housing 4 by means of plain bearings instead of antifriction bearings 14. The rotational motion of the drive shaft 2 is transformed in to the rotatively oscillating motion of the second shaft 5 by the gear mechanism 1.

The gear mechanism 1 comprises a longitudinal lever 9, disposed transversely to the longitudinal axis 3, with a central axis 13, a middle segment 30 and two ends 10; 11, the lever 9 being firmly connected in its middle section 30 with a pivot 6, which is disposed terminally and eccentrically at the gear mechanism side at the drive shaft 2 so that it can be rotated about the axis 7 of the pivot, a first cam 15, fixed firmly to the housing 4, and a catch 12, which is connected firmly with the second shaft 5 and the central axis 19 of which is perpendicular to the longitudinal axis 3 at a distance "a" from the latter. Furthermore, the first cam 15 is firmly connected with the housing 4 and, measured at right angles to the longitudinal axis 3, is at a distance b from the latter. The ends 10; 11 of the lever 9 are fork-shaped, each prong of the fork having a terminal, open, longitudinal guide 16; 17, which is disposed parallel to the central axis 13 of the lever 9. The first guide 16 is mounted at the fixed cam 15 so that it can be shifted parallel to the central axis 13 of the lever 9 and rotated about the central axis 19. Furthermore, the catch 12 is equipped with a second cam 18. The second guide 17 is mounted so that it can be shifted at the second cam 18 parallel to the central axis 13 of the lever 9 and rotated about the central axis 20 of the second cam 18. Measured at right angles to the longitudinal axis 3, the pivot 6 has an eccentricity e and is mounted so that it can be rotated about the axis 7 of the pivot 6 in the central borehole 8 of the lever 9, disposed parallel to the longitudinal axis 3 and perpendicularly to the central axis 13 of the lever 9.

When the drive shaft 2 is rotated, the lever 9 is moved by the eccentric pivot 6. The lever 9 is guided by the displaceable seating of the first cam 15 in the first guide 16 at the second end 11 of the lever 9, so that the central axis 13 of the lever 9 always intersects the central axis 19 of the second cam 18. The movement of the lever 9 accordingly is a superimposition of a displacement parallel to the central axis 13 of the lever 9 and a rotative oscillational movement about the central axis 19 of the second cam 18. By these means, the central axis 20 of the second cam 18 is moved with an angle of rotation of $\pm\alpha$, the angle of rotation $\alpha$ depending on the dimensions of "a", b and e and falling within a range of 0.05° to 10°.

Furthermore, the drive shaft 2, including the pivot 6, as well as the second oscillating shaft 5 are each provided with a continuous central borehole 26; 27, which is coaxial with the longitudinal axis 3, so that a guide wire, previously fixed at a bone, can be introduced into the central boreholes 26; 27, as a result of which the device can be positioned accurately for the task, which is to be carried out, such as a sawing task.

Figure 3A:
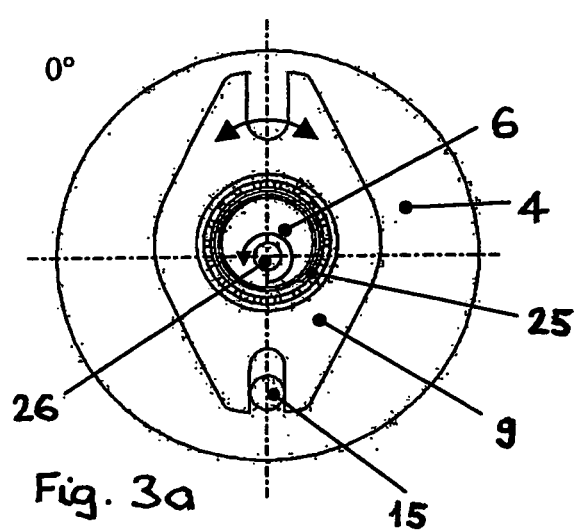
FIG. 3a shows a section through an embodiment of the inventive device, perpendicular to the longitudinal axis, the drive shaft being in its initial position, that is, at an angle of rotation of 0°.
Figure 3B:
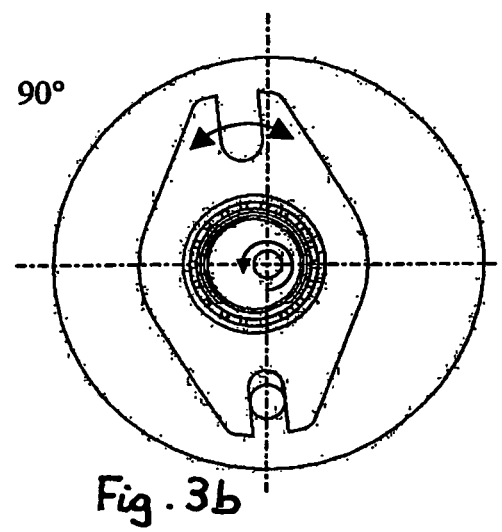
FIG. 3b shows a section through the embodiment of the inventive device, shown in FIG. 3a, perpendicular to the longitudinal axis, the drive shaft having an angle of rotation of 90°.
Figure 3C:
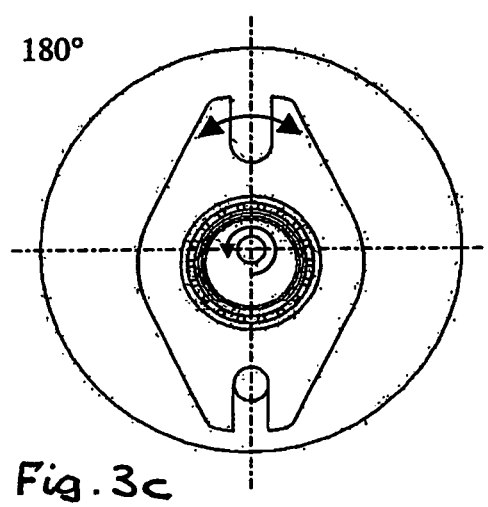
FIG. 3c shows a section through the embodiment of the inventive device, shown in FIGS. 3a and 3b, perpendicular to the longitudinal axis, the drive shaft having an angle of the rotation of 180°.
Figure 3D:
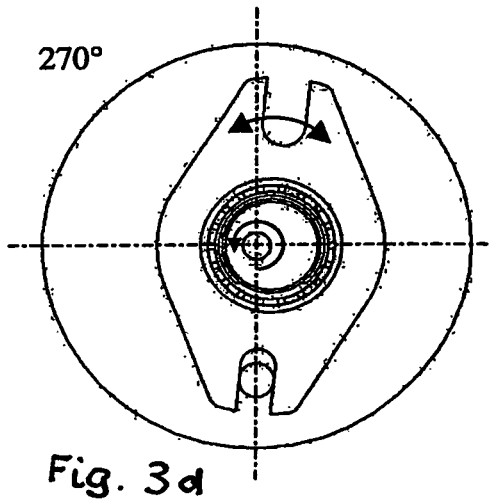
FIG. 3d shows a section through the inventive device shown in FIGS. 3a to 3c, perpendicular to the longitudinal axis, the drive shaft having an angle of rotation of 270°.

The embodiment of the inventive device, shown in FIGS. 3a to 3d, differs from that shown in FIGS. 1 and 2 only in that the lever 9 is mounted rotatably at the pivot 6 by means of an antifriction bearing 25, which is introduced into the central borehole 8 of the lever 9 (FIG. 1). Furthermore, the drive shaft 2 in FIG. 3a is in its starting position, that is, the angle of rotation is 0°. In FIG. 3b, the drive shaft 2 is shown at an angle of rotation of 90° and, in FIGS. 3c and 3d, it is shown at angles of rotation of 180° and 270° respectively.

Figure 4:
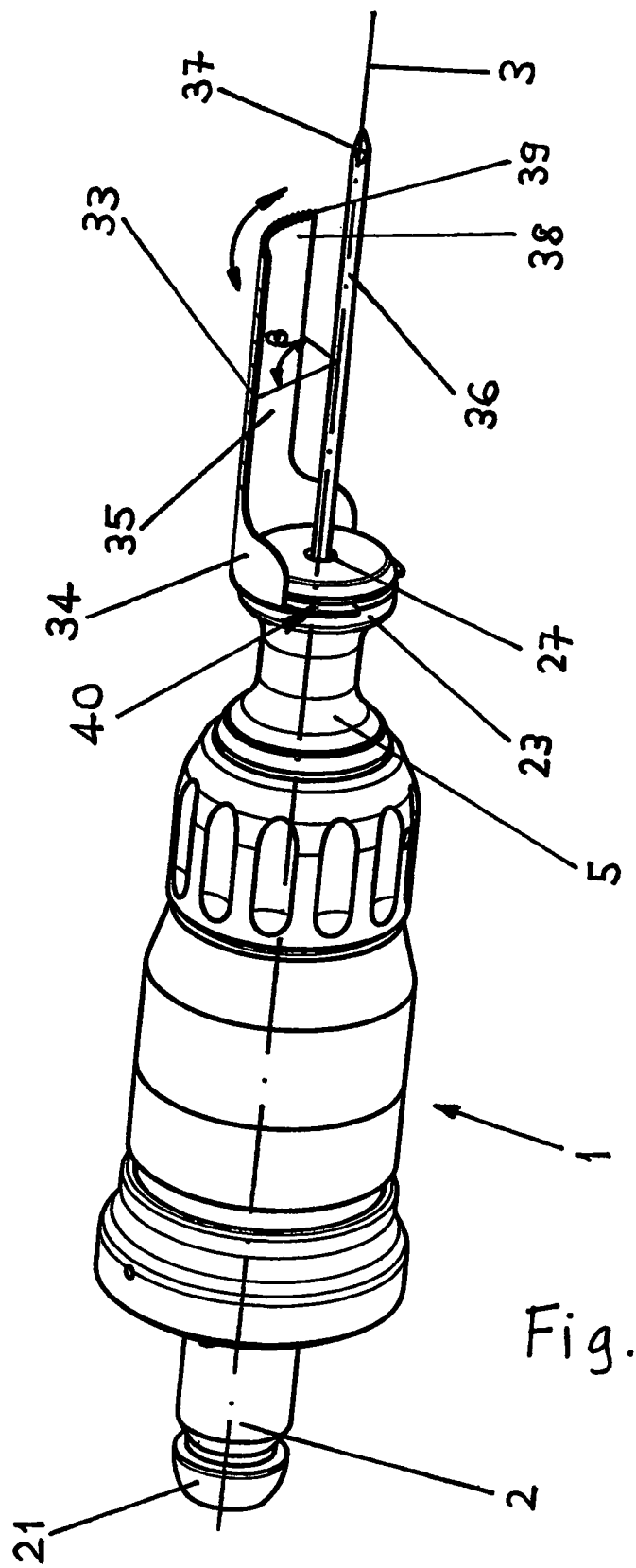
FIG. 4 shows a perspective view of an embodiment of the inventive sawing device.

In FIG. 4, an embodiment of the inventive sawing device is shown which comprises, aside from a gearing mechanism 1 as shown, for example, in FIGS. 1 to 3, a saw blade 35 and a guide wire 36. The guide wire 36 is introduced into the central boreholes 26; 27 (FIG. 1), which pass coaxially through the gearing mechanism 1 as well as through the drive shaft 2 and the second shaft 5, so that its tip 37 protrudes axially over the front end 38 of the saw blade 35, which is provided with the saw teeth 39. The saw blade 35, as a hollow cylindrical shell piece coaxial with the longitudinal axis 3, is equipped with an annular segment-shaped cross-sectional area, orthogonal to the longitudinal axis 3. The central angle $\beta$ of the annular segment-shaped cross-sectional area is about 90° here. The saw teeth 39 are mounted at the front end 38 of the saw blade 35, so that a circular saw cut, concentric with the longitudinal axis 3, can be produced in a bone or bone fragment by the saw blade. At the front end 23 of the second shaft 5, means 40 are mounted for detachably the fastening the saw blade 35 and may be configured as a bayonet catch or a threaded connection. The drive shaft 2 of the gearing mechanism 1 is driven by a motor (not shown), which can be coupled at the rear end 21 of the drive shaft 2. Consequently, the rotational movement of the drive shaft 2 is converted into an oscillating movement by the gearing mechanism 1, so that the saw blade 35, which is disposed at the front end 23 of the second shaft 5, carries out an oscillating rotational movement, concentric with the longitudinal axis 3. Furthermore, a scale 33, on which the depth of the saw cut, which has been produced, and which is parallel to the longitudinal axis 3, is mounted on the outer shell surface 34 of the saw blade 35.

What is claimed:
1. A device for treating a body site, comprising:
a drive shaft having a longitudinal axis, a rear end associable with a drive unit, a front end, a central borehole, and a pivot at the front end eccentrically disposed with respect to the longitudinal axis of the drive shaft and having a central axis parallel to and offset from the longitudinal axis of the drive shaft;

an oscillating shaft having a longitudinal axis, a central borehole, a front end associable with a surgical tool or instrument, and a rear end;

a mechanism disposed between the front end of the drive shaft and the rear end of the oscillating shaft, for converting a rotational movement of the drive shaft into an oscillating rotational movement of the oscillating shaft concentric with the longitudinal axis of the oscillating shaft; and a guide wire configured to extend through the central boreholes of the drive shaft and the oscillating shaft, wherein the longitudinal axes of the drive shaft and the oscillating shaft are substantially coaxial.

2. The device of claim 1, wherein the mechanism comprises a movable lever substantially transverse to the longitudinal axis of the drive shaft.

3. The device of claim 2, wherein the movable lever is fixedly connected to the pivot.

4. The device of claim 1, wherein at least a portion of both the drive shaft and the oscillating shaft are disposed in a housing.

5. The device of claim 1, wherein the surgical tool or instrument is detachably fastened to the oscillating shaft.

6. The device of claim 1, wherein the surgical tool or instrument has an axis substantially parallel to the longitudinal axis of the drive shaft.

7. The device of claim 1, wherein the mechanism causes the oscillating shaft to oscillate at an angle between about 0.05° and about 10°.

8. A device for positioning and operating a surgical tool or instrument, comprising:

a drive shaft having a longitudinal axis, a front end, a central borehole, and a pivot eccentrically disposed relative to the longitudinal axis of the drive shaft, the pivot having a central axis parallel to and offset from the longitudinal axis of the drive shaft;

an oscillating shaft having a longitudinal axis, a central borehole, a front end associable with a surgical tool or instrument, and a rear end;

a movable lever substantially transverse to the longitudinal axis of the drive shaft and connected to the pivot; and a guide wire configured to extend through the central boreholes of the drive shaft and the oscillating shaft;

wherein the oscillating shaft is connected to a catch, and wherein the movable lever engages the catch to rotationally oscillate the oscillating shaft concentric with the longitudinal axis of the oscillating shaft;

wherein the device is configured to be lowered over the guide wire to position the device in relation to a body site;

wherein the longitudinal axes of the drive shaft and oscillating shaft are substantially coaxial.

9. The device of claim 8, wherein the surgical tool or instrument has an axis substantially parallel to the longitudinal axis of the drive shaft.

10. The device of claim 8, wherein the surgical tool or instrument is detachably fastened to the oscillating shaft.

11. The device of claim 8, wherein the movable lever comprises a recess for receiving at least a portion of the pivot.

12. The device of claim 8, wherein at least a portion of both the drive shaft and the oscillating shaft are disposed in a housing.

13. A device for treating a body site, comprising:

a drive shaft having a longitudinal axis, a rear end associable with a drive unit, a front end, and a pivot eccentrically disposed relative to the longitudinal axis of the drive shaft, the pivot being located at the front end of the drive shaft and having a central axis parallel to and offset from the longitudinal axis of the drive shaft;

an oscillating shaft having a longitudinal axis, a front end associable with a surgical tool or instrument, and a rear end;

a mechanism disposed between the front end of the drive shaft and the rear end of the oscillating shaft, for converting a rotational movement of the drive shaft into an oscillating rotational movement of the oscillating shaft concentric with the longitudinal axis of the oscillating shaft; and a guide element substantially parallel to the longitudinal axis of the drive shaft, wherein the longitudinal axes of the drive shaft and the oscillating shaft are substantially coaxial.

14. The device of claim 13, wherein the drive shaft and the oscillating shaft each further comprise a central borehole, and wherein the guide element extends through the central boreholes.

15. The device of claim 13, wherein the guide element comprises a guide wire.

* * * * *